US00PP08387P

United States Patent [19]

Akerboom

[11] Patent Number: Plant 8,387

[45] Date of Patent: Sep. 21, 1993

[54] ASTER PLANT NAMED PURPLE MONARCH

[76] Inventor: Petrus J. F. Akerboom, Paradijsweg 61, 2461 TL, Ter Aar, Netherlands

[21] Appl. No.: 895,726

[22] Filed: Jun. 9, 1992

[51] Int. Cl.[5] ..... A01H 5/00

[52] U.S. Cl. ..... Plt./68.1

[58] Field of Search ..... Plt./68.1

*Primary Examiner*—James R. Feyrer

*Attorney, Agent, or Firm*—Foley & Lardner

[57] ABSTRACT

A distinct cultivar of aster plant named 'Purple Monarch', characterized by its cupped capitulum form, daisy capitulum type, deep violet ray floret color, capitulum diameter of 32–35 mm, strong, well branched flower stems, and its many flowers borne on short pedicels.

1 Drawing Sheet

The present invention comprises a new and distinct cultivar of Aster L. hereinafter referred to by the cultivar name 'Purple Monarch'.

'Purple Monarch' is a product of a planned breeding program which had the objective of creating new perennial Aster cultivars for year-round commercial production having well branched flower stems, large flower (capitulum) size, good flower (capitulum) form and shape, and having superior lasting quality of the cut flowers. Such traits in combination were not present on needed improvement in previously available commercial cultivars.

'Purple Monarch' was originated from a hybridization made by the inventor P. Akerboom in a controlled breeding program in Ter Aar, The Netherlands, in 1987. The female parent of 'Purple Monarch' was an unnamed *Aster pilosus* seedling. The male parent was an unnamed *Aster novi-belgii* seedling.

'Purple Monarch' was discovered and selected as one flowering plant within the progeny of the stated parentage by the inventor P. Akerboom on Sep. 10, 1987 in a controlled environment in Ter Aar and identified as seedling No. 87.M.K.B.D.Bl.E.G.

The first act of asexual reproduction of 'Purple Monarch' was accomplished when vegetative cuttings were taken from the initial selection in November 1987 in a controlled environment in Ter Aar by a technician working under formulations established and supervised by P. Akerboom.

Horticultural examination of selected units initiated in 1988 and 1989 has demonstrated that the unique combination of characteristics as herein disclosed for 'Purple Monarch' are firmly fixed and are retained through successive generations of asexual reproduction.

'Purple Monarch' has not been observed under all possible environmental conditions. The phenotype may vary significantly under different environmental conditions of temperature, light intensity and daylength, without, however, any variance in the genotype.

The following observations, measurements and comparisons describe plants grown in Ter Aar under greenhouse conditions which approximate those generally used in commercial greenhouse practice in this country. The following traits have been repeatedly observed and are determined to be basic characteristics of 'Purple Monarch', which, in combination, distinguish this Aster as a new and distinct cultivar:

1. Cupped capitulum form.
2. Daisy capitulum type.

3. Violet ray floret color.
4. Diameter across face of capitulum of 32 to 35 mm at maturity.
5. Strong, well branched flower stems.
6. Many capitula per synflorescence, borne on short pedicels.

The accompanying color photographic drawings show typical synflorescence of 'Purple Monarch', with the colors being as nearly true as possible with illustrations of this type.

The color photograph at the top of the sheet is a perspective view of 'Purple Monarch' grown as a single stem cut spray Aster.

The photograph at the bottom of the sheet comprises a top view of four flowers. It should be noted that the actual ray floret color of 'Purple Monarch' is accurately expressed in the color values below, but is not present in the photographs.

Of the commercial cultivars known to the inventor, the most similar to 'Purple Monarch' is the variety 'Blue Butterfly', disclosed in U.S. Plant Pat. No. 7,399. Reference is made to attached Chart A, which compares certain characteristics of 'Purple Monarch' to the same characteristics of 'Blue Butterfly'.

In comparison to 'Blue Butterfly', 'Purple Monarch' has more vigorous growth, thicker and courser flower stems, shorter and broader leaves, larger flowers (capitula) of a deep violet color, and many more ray florets. Similar traits are capitulum form and type, spray formation, photoperiodic light reaction, and equally long lasting vase-lifes.

When compared to the male parent's flower and flower stem characteristics, 'Purple Monarch' is much easier to handle during harvesting. *Novi-belgii* cultivars are typically brittle and have easy breaking flower heads and branching stems. 'Purple Monarch' is absolutely free of these drawbacks.

In the following description color references are made to the Royal Horticultural Society Colour Chart. The color values were determined between 12:00 and 14:00 hours on Jun. 20, 1989 at Ter Aar, The Netherlands.

Classification:

*Botanical.*—*Aster pilosus*×*novi-belgii* cv 'Purple Monarch'.

*Commercial.*—Medium, daisy-like spray Aster perennial.

INFLORESCENCE

A. Capitulum:

*Form.*—Cupped.

*Type.*—Daisy.

*Diameter across face.*—31 to 35 mm.

*Arrangement.*—Raceme inflorescence.

B. Corolla of ray florets:

*Color (general tonality from a distance of three meters).*—Purple.

*Color (upper surface).*—Closest to 86B.

*Color (under surface).*—Closest to 86B.

*Shape of floret.*—Apex acute; very short to short, narrow obovate, straight.

*Size of floret.*—15-16 mm long×4-5 mm wide.

*Number of ray florets.*—28-35.

C. Corolla of disc florets:

*Color (mature).*—Closest to 1C/1D.

*Color (immature).*—Closest to 1C/1D.

*Diameter of disc.*—8-9 mm.

D. Reproductive organs:

*Androecium.*—Present on disc florets only; little to very little pollen.

*Gynoecium.*—Present on both ray and disc florets.

PLANT

A. General appearance:

*Height.*—Tall; depends on light reaction; under continuous long days it can grow up to two meters tall; medium branching.

B. Foliage:

*Color.*—147A.

*Shape.*—Lanceolate to oblanceolate.

*Size.*—Lower leaves, length 160-180 mm, short; width 35-37 mm, very broad. Upper leaves, length 110 mm; width 23 cm.

*Margin.*—Dentate over entire margin.

*Arrangement.*—Alternate, with angle recurvate.

CHART A
Comparison of 'Purple Monarch' and 'Blue Butterfly'

| Cultivar | PURPLE MONARCH | BLUE BUTTERFLY |
|---|---|---|
| Ray floret color | Purple | Blue |
| Capitulum form and type | Cupped daisy | Cupped daisy |
| Spray formation | Compound | Compound |
| Pedicels | 2-45 mm long | 8-18 mm long |
| Diameter across face of capitulum | 31-35 mm | 27-30 mm |
| Number of ray florets | 31-35 | 27-29 |

I claim:

1. A new and distinct cultivar of aster named 'Purple Monarch', as illustrated and described.

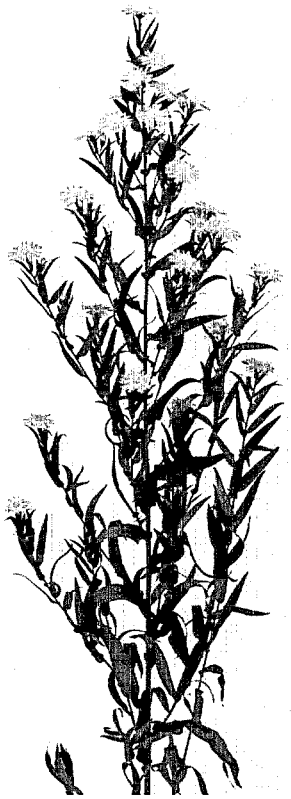
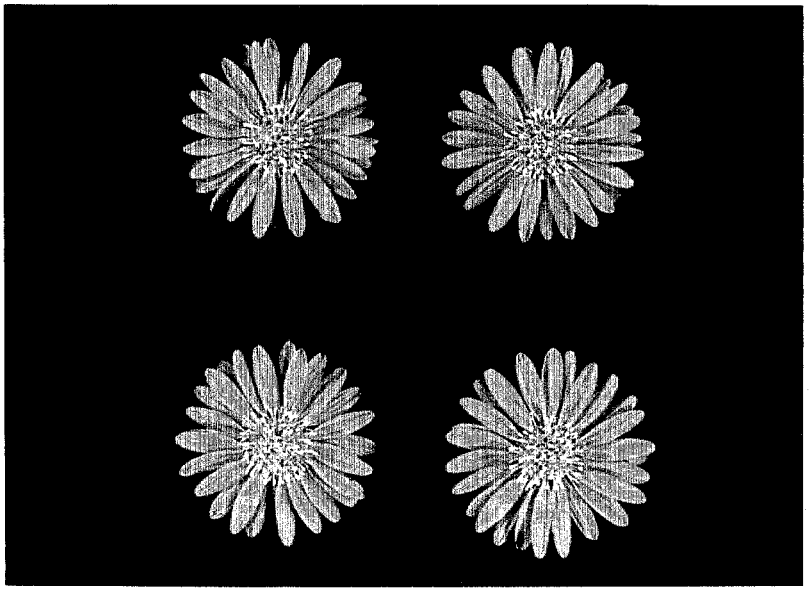

* * * * *